(12) United States Patent
Moslemy et al.

(10) Patent No.: US 9,539,141 B2
(45) Date of Patent: Jan. 10, 2017

(54) SYSTEM AND METHOD FOR OCULAR IONTOPHORESIS WITH BUFFERING

(71) Applicant: Eyegate Pharmaceuticals, Inc., Waltham, MA (US)

(72) Inventors: Peyman Moslemy, Mansfield, MA (US); Michael Manzo, Beverly, MA (US); William Schubert, Chelmsford, MA (US); William Isom, Maynard, MA (US); Pierre Roy, Paris (FR)

(73) Assignee: Eyegate Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 14/930,193

(22) Filed: Nov. 2, 2015

(65) Prior Publication Data

US 2016/0120696 A1    May 5, 2016

Related U.S. Application Data

(63) Continuation of application No. 13/141,810, filed as application No. PCT/US2009/069580 on Dec. 28, 2009, now Pat. No. 9,180,292.
(Continued)

(51) Int. Cl.
*A61F 9/00* (2006.01)
*A61N 1/04* (2006.01)
(Continued)

(52) U.S. Cl.
CPC .......... *A61F 9/0026* (2013.01); *A61N 1/0444* (2013.01); *A61N 1/303* (2013.01); *A61N 1/325* (2013.01); *A61N 1/0448* (2013.01)

(58) Field of Classification Search
CPC ..... A61F 9/0026; A61N 1/303; A61N 1/0444; A61N 1/325; A61N 1/0448
See application file for complete search history.

(56) References Cited

U.S. PATENT DOCUMENTS 9,180,292 B2 * 11/2015 Moslemy ............. A61N 1/0444
2005/0197618 A1    9/2005 Plummer et al.
2007/0123814 A1 *  5/2007 Roy ..................... A61N 1/0424
                                                    604/20

OTHER PUBLICATIONS

Office Action from related Canadian Patent Application No. 2,750,149 mailed Feb. 12, 2016.

* cited by examiner

*Primary Examiner* — Emily Schmidt
*Assistant Examiner* — Lauren M Peng
(74) *Attorney, Agent, or Firm* — Burns & Levinson LLP; Joseph M. Maraia (57) ABSTRACT

Compositions, devices, method of manufacture, and methods of delivery of a therapeutic substance across a surface of an eyeball via iontophoresis including a therapeutic media reservoir and a buffer system within an iontophoretic chamber. When energized, an electrode provides and electromotive force that transfers a dosage of the therapeutic substance from the iontophoretic chamber across the surface of the eyeball. The buffering system includes a buffer media and at least on buffer element, or agent that regulates pH during iontophoretic transfer of the therapeutic substance. The buffer media includes at least one of a foam, a gel (solid or liquid), a membrane, and a plurality of multi-particulates. The buffer media can be included within the iontophoretic chamber, together with the therapeutic media reservoir, in various arrangements including on or more layers and one or more concentric cylinders.

19 Claims, 8 Drawing Sheets

Related U.S. Application Data (60) Provisional application No. 61/180,602, filed on May 22, 2009, provisional application No. 61/141,994, filed on Dec. 31, 2008.

(51) Int. Cl.
*A61N 1/30* (2006.01)
*A61N 1/32* (2006.01)

SYSTEM AND METHOD FOR OCULAR IONTOPHORESIS WITH BUFFERING

RELATED APPLICATIONS

This application is a continuation of U.S. application Ser. No. 13/141,810 filed Aug. 4, 2011, which is a U.S. National Application of PCT/U.S. 2009/069580, filed Dec. 28, 2009 which claims benefit of U.S. provisional Application No. 61/141,994, filed Dec. 31, 2008, and U.S. Provisional Application No. 61/180,602, filed May 22, 2009, the entire contents of each of which are incorporated herein by reference.

FIELD

The technology described herein is generally related to a system and process for ophthalmic transfer of a therapeutic substance across a surface of an eyeball via iontophoresis. In some embodiments, the technology is related to buffering systems and methods that regulate pH of therapeutic substances during iontophoresis.

BACKGROUND

Ocular iontophoresis is the application of an electrical source to propel charged and/or active molecules from a reservoir into the intraocular tissues of a mammal, including a human or an animal. Positively charged ions can be driven into the ocular tissues by electro-repulsion at the anode while negatively charged ions are repelled from the cathode. The simplicity and safety of iontophoretic application includes enhanced targeted delivery of compound(s) of interest, and the reduction of adverse side effects have resulted in extensive use of iontophoresis in laboratory, clinical research and commercial use. Unlike ocular injections (intravitreal, retrobulbar, and peribulbar) and intraocular implants, iontophoresis is a noninvasive technique used to deliver compounds of interest into the anterior and/or posterior compartments of the eye. Iontophoretic delivery can be used to obtain intraocular concentrations and residence times that are equal to or greater than those achieved by conventional modalities such as topical drops, ointments, and gels.

Iontophoresis has been widely used in dermal applications in which therapeutic compounds are transported across a patient's skin using electrical currents. Due to the relative high impedance of the skin, the electrical currents are generally relatively low. Consequently, dosage times tend to be relatively long, for example being greater than an hour. In such applications, iontophoresis can be applied to the patient's skin with an active drug-containing adhesive patch Ocular iontophoresis devices are typically constituted by a direct current (DC) electric field source coupled to two electrodes, referred to respectively as "active" and "passive" electrodes. The active electrode provides an electromotive force, when energized, that acts on an electrolyte containing therapeutic composition(s) to transfer one or more therapeutic substance(s) across a surface of the eyeball, while the passive electrode serves as a return electrode and enables the electric circuit to be looped through the patient's body. The compound of interest is transported via the active electrode across the tissue when a current is applied to the electrodes through the tissue. Compound transport may occur as a result of a direct electrical field effect (e.g., electrophoresis), an indirect electrical field effect resulted from the bulk volume flow of solution from the anode to cathode (e.g., electroosmosis), electrically induced pore or transport pathway formation (e.g., electroporation), or a combination of any of the foregoing. Examples of currently known iontophoretic devices and methods for ocular drug delivery may be found in the U.S. Pat. Nos. 7,164,943; 6,697,668; 6,319,240; 6,539,251; 6,579,276; 6,697,668, and PCT publications WO 03/030989 and WO 03/043689, each of which is incorporated herein by reference.

Ocular iontophoresis, however, presents several unique challenges. For example, the applicator must conform to the spheroidal geometry of the eyeball. That is, the portion of the applicator in contact with a surface of the eye must be specifically formed to minimize loss of therapeutic substance and to reduce discomfort. Also, since the electrical impedance of the eye is relatively lower than that of the epidermis, higher currents can be achieved at still reasonably low current densities. Accordingly, dosage times tend to be relatively short, often much less than one hour.

SUMMARY

Iontophoretic transfer of a therapeutic substance may result in unwanted changes in pH that result in patient discomfort, and in some instances, tissue damage. There remains a need to regulate the pH of a therapeutic preparation within the physiologically acceptable range during iontophoresis while maintaining the therapeutic substance at the highest ionization state for optimal delivery. Further, there remains a need to improve the delivery efficiency of a therapeutic substance while reducing the risks of any possible damage (e.g., irritation or burning of tissues) that could limit the use of ocular iontophoresis. The present technology is related to buffering systems and methods that regulate pH of therapeutic substances during iontophoresis while improving delivery efficiency and safety.

In one embodiment, a delivery device for transferring a therapeutic substance across and/or through a surface of an ocular globe includes at least one iontophoretic chamber configured to store the therapeutic substance. The device also includes an electrode disposed relative to the at least one iontophoretic chamber. The electrode is configured to provide an electromotive force that, when energized, transfers at least a portion of the therapeutic substance stored within the iontophoretic chamber across the surface of the ocular globe. A buffer system is disposed at least partially within the at least one iontophoretic chamber. The buffer system is configured to regulate the pH of the therapeutic substance and to maintain the pH at the surface of the ocular globe within a range of about 3 to 8 during iontophoretic transfer of the therapeutic substance.

In one embodiment, the buffer system can be a buffering agent to reduce the risk of damage to ocular tissue. The buffer agent can be at least one of an ion exchange resin, polymeric particles, insoluble buffer particles, cationic particles, anionic particles and zwitterionic particles. The ion exchange resin can be at least one ion exchange material having a characteristic nature of at least one of a strong acid, a strong base, a weak acid, and a weak base. In one embodiment, the buffer system can further include a therapeutic substance.

In one embodiment, the pH can be maintained at a level substantially equal to the highest ionization level of the therapeutic substance to enhance transport efficiency of the therapeutic substance. In another embodiment, the buffer system can be electrically conductive capable of conducting an electric field supplied from the electrode.

In one embodiment, the buffer system can be at least one of a porous material, a liquid solution, a gel, a packed bed resin, a hydrogel film, and membrane. The porous material can be at least one of a foam, a fabric, a nonwoven material, and a sintered material. The gel can be at least one of a hydrogel matrix and an aerogel matrix. The membrane can be at least one of a mono-laminar, a multi-laminar film, hydrophobic (semi permeable) membrane, and a non-permeable/solid membrane.

In one embodiment, the iontophoretic chamber can further include at least a first layer and at least a second layer, the first layer including the buffer system and the second layer including a therapeutic substance. The first layer can be disposed between the electrode and the second layer. In another embodiment, the iontophoretic chamber can further include a membrane disposed between the first layer and the second layer. The membrane can have a low water vapor permeability to maintain water content in each layer. In yet another embodiment, the layers can be concentrically relative to each other. The membrane can be disposed between the first layer and the second layer. In another embodiment, the first layer can have a higher buffering capability than the second layer.

In one embodiment, the iontophoretic chamber can further include a first layer, a second layer, and a third layer, the first layer and the second layer including the buffer system and the third layer including a therapeutic substance. The first layer can be disposed closest to the electrode and the second layer is disposed between the first layer and the third layer. In another embodiment, the iontophoretic chamber can further include a membrane disposed between the first layer and the second layer or the second layer and the third layer. The membrane has low water vapor permeability to maintain water content in each layer. In yet another embodiment, the layers can be arranged concentrically relative to each other. The membrane can be between the first layer and the second layer or the second layer and the third layer. In another embodiment, the third layer can include the therapeutic substance is removeably coupled to the iontophoretic chamber, the first layer can have a higher buffering capability than the second layer, and/or the second layer can include a ionic composition that optimizes electro-transport of the therapeutic substance in the third layer.

In another embodiment, the buffer system can be arranged as a buffered surface coating. The buffer system can further include a rehydrating agent. The buffer system can be disposed adjacent to the electrode.

In another embodiment, a process for transferring a therapeutic substance across a surface of an ocular globe includes positioning a delivery device directly to the surface of an ocular globe. The delivery device includes at least one iontophoretic chamber storing at least one therapeutic substance. A potential is applied to an active electrode disposed relative to the iontophoretic chamber to iontophoretically transfer a portion of the at least one therapeutic substance across the adjacent surface of the ocular globe. The buffer system is configured to regulate the pH of the therapeutic substance and to maintain the pH at the surface of the ocular globe within a range between about 3 and about 8 during iontophoretic transfer of the therapeutic sub stance.

In another embodiment, an ocular iontophoresis device for transferring a dosage of therapeutic substance across and/or through a surface of an eyeball, includes an iontophoretic chamber with an open end configured to be positioned on the surface of the eyeball. A reservoir medium is disposed within the iontophoretic chamber, configured to retain a therapeutic substance. The device also includes an electrode positioned with respect to the iontophoretic chamber, to provide an electromotive force, that when energized, transfers the dosage of therapeutic substance across the surface of the eyeball. A buffer system is disposed within the iontophoretic chamber, containing at least one buffer element configured to regulate pH change during iontophoretic transfer of the dosage of therapeutic substance within a range between about 3 and about 8.

In another embodiment, a process for manufacturing an ocular iontophoresis device includes providing an iontophoretic chamber having an open end configured to be positioned on a surface of an eyeball. A reservoir medium is located within the iontophoretic chamber. The reservoir medium contains a therapeutic substance deliverable to the eyeball. An electrode is arranged opposite the open end of the iontophoretic chamber. The electrode is associated with the iontophoretic chamber to provide an electromotive force, when energized, that transfers a dosage of the therapeutic substance across the surface of the eyeball. A buffer system is located within the iontophoretic chamber. The buffer system is configured to regulate the pH of the therapeutic substance and to maintain the pH at the surface of the ocular globe within within a range between about 3 and about 8 during iontophoretic transfer of the therapeutic substance.

In yet another embodiment, a process for transferring a dosage of therapeutic substance across and/or through a surface of an eyeball includes positioning an open end of an iontophoretic chamber including a therapeutic substance onto the surface of the eyeball. An electrical potential is applied to the iontophoretic chamber to induce transfer of the dosage of therapeutic substance across the surface of the eye. Change of pH of the therapeutic substance is regulated within a range between about 3 and about 8 during an extended period during which the dosage of therapeutic substance is transferred. Regulation of the pH change is accomplished using a buffer system.

BRIEF DESCRIPTION OF THE DRAWINGS

The foregoing and other objects, features and advantages of the invention will be apparent from the following more particular description of preferred embodiments of the invention, as illustrated in the accompanying drawings.

In the drawings, identical reference numbers may identify similar elements or acts. The shapes, sizes, and relative positions of device elements in the drawings are not necessarily precise or drawn to scale. For example, the shapes and sizes of elements may not be drawn to scale, and/or one or more of the elements may be arbitrarily enlarged or positioned to improve drawing legibility. Furthermore, the particular shapes of the elements as drawn are not intended to convey any information regarding the actual shape of the particular elements, and have been solely selected for ease of recognition in the drawings.

DEFINITIONS

The terms 'therapeutic substance' and 'active pharmaceutical ingredient (API)' are used interchangeably throughout the specification, and by definition refer to a substance intended for use in the diagnosis, cure, mitigation, treatment, or prevention of a disease of the eye. Such substance is intended for use as a component of a medicine, and in some embodiments of this invention a component, part, or accessory of an iontophoresis device.

The terms 'therapeutic preparation', 'therapeutic composition' and 'drug preparation' are used interchangeably throughout the specification, and by definition refer to a product of mixing or combining various pharmaceutically acceptable active and inactive elements or ingredients.

DETAILED DESCRIPTION

As described herein, various embodiments of compositions, devices, methods of use and methods of manufacture for ophthalmic transfer of a therapeutic substance across a surface of an eyeball via iontophoresis are directed to achieve at least one (e.g., principle) objective of buffering the therapeutic substance to a biologically acceptable pH range during iontophoretic treatment. An additional objective of at least some of the various embodiments is to maximize electro-transport delivery of the therapeutic substance by maintaining the pH to achieve the highest ionization level of the therapeutic substance. Another benefit of maintaining the pH of the therapeutic substance is a consistent/predictable dose delivery. Yet another objective of at least some of the various embodiments is to increase the delivery of the therapeutic substance(s) to the eye by reducing the amount of competing ions, and to maintain the stability of the therapeutic substance(s) during iontophoretic treatment and storage.

Figure 1A:
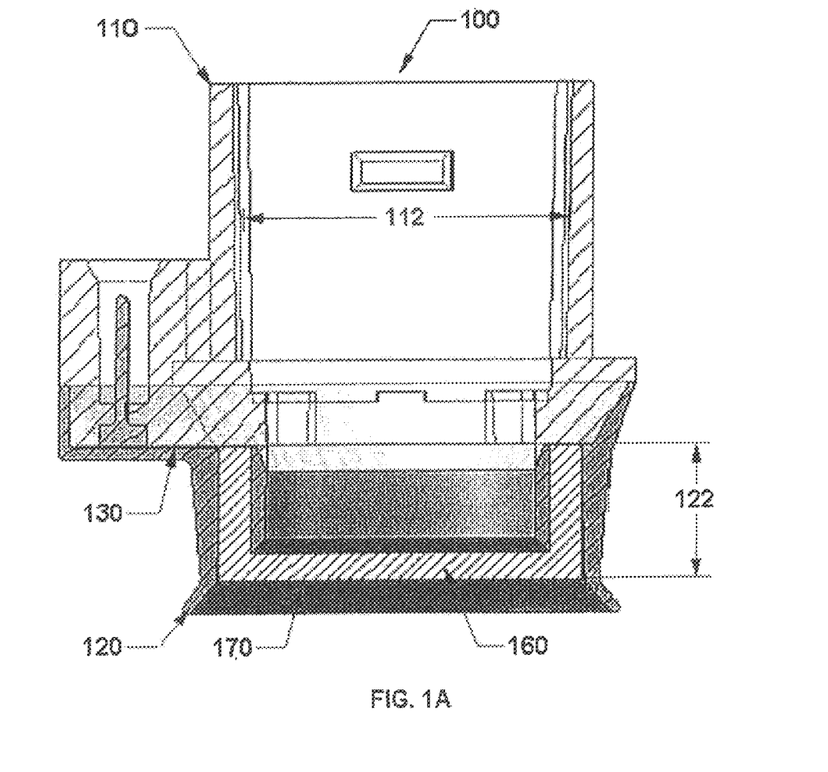
FIG. 1A shows a longitudinal cross section of a single layer buffered reservoir ocular iontophoresis device.
Figure 1B:
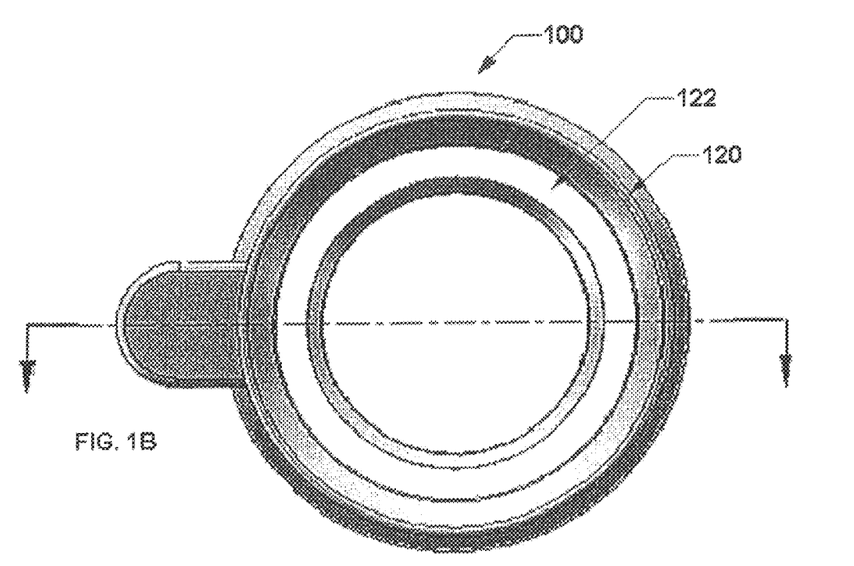
FIG. 1B shows a distal-end view of the ocular iontophoresis device shown in FIG. 1A.

FIGS. 1A-1B show an exemplary single layer buffered reservoir ocular iontophoresis device 100 for buffering a therapeutic substance to a biologically acceptable pH range at the surface of an eyeball being treated during iontophoretic treatment. The ocular iontophoresis device 100 includes a distal end 110 and a proximal end 120. The distal end 110 defines a cavity 112 for receiving the therapeutic substance. The proximal end 120 defines an annular reservoir 122 (iontophoretic chamber) for delivering the therapeutic substance to the ocular area of the eyeball surface. The ocular area is typically a part of the sclera of the eyeball. An active electrode 130 is disposed between the distal end 110 and the proximal end 120; and is typically disposed at the beginning of the annular reservoir 122. In one embodiment, a buffer system 160 containing a buffering agent and/or the therapeutic substance can be disposed in the annular reservoir 122. In one embodiment, the therapeutic substance can be an active pharmaceutical ingredient (API).

The addition of the buffering system 160 to the iontophoretic chamber 122 allows the iontophoresis device to self-buffer. A self-buffering iontophoresis device reduces the risk of damage to ocular tissue as a result of dramatic pH changes that can occur in a non-buffered system.

The buffer system 160 is configured to provide a buffer action that maintains pH within the vicinity of a treatment surface 170, within a biocompatible range, during the duration of delivery of a dose. The treatment surface 170 is the area of the annular reservoir that contacts or is in close contact with the surface of the eyeball. The biocompatible range of pH for ocular delivery may depend upon the individual, but is generally within the range of about 3 to about 8. In a preferred embodiment, the biocompatible range of pH is maintained within a range of about 3 to about 7 throughout the duration of delivery. Even more preferably, the pH is maintained at a level equal to the highest ionization level of the therapeutic substance in order to enhance transport efficiency of the therapeutic substance.

In some embodiments, the buffer system 160 can be electrically conductive medium capable of conducting an electric field supplied by the active electrode 130 to deliver the therapeutic substance. In other embodiments, the buffer system 160 can be disposed in electrical conductive medium. Additional exemplary embodiments of the buffer system 160 are further described below including a porous material, a buffered gel (liquid or solid), a packed bed resin (ion exchange resin), a hydrogel film or membrane, and combinations of any of these components.

As described above, in one embodiment, the annular reservoir or iontophoretic chamber 122 includes a buffer system 160. The buffer system 160 includes a buffer medium having at least one buffer agent (composition) and a therapeutic substance, such as an active pharmaceutical ingredient (API). In some embodiments, the buffer medium includes one or more porous materials for containing a preparation (e.g., API, inactive ingredients, buffer, etc.). The API preparation may be a liquid solution preparation. The liquid solution preparation may include one or more therapeutic substances together with a buffering composition. At least one of the therapeutic substances may be dissolved in a liquid solution preparation. Likewise, the buffering composition may also include a soluble buffer composition. The porous material may be saturated with the liquid solution preparation. In such embodiments, the iontophoretic chamber 122 may contain a buffer medium and an API, each within the same porous material, such as, for example, foam, containing a solution preparation of the one or more therapeutic substances and buffer.

In some embodiments, the API medium itself provides a buffering action sufficient to maintain pH at the point of contact between the device 100 and the eye within a preferred range, including any of the pH ranges described herein. The ability of an API to act as a buffering agent arises from its acid-base dissociation constants ($pKa_1$, $pKa_2$, etc.). The pKa distributions of drugs are influenced by the nature and frequency of occurrence of the functional groups that are commonly observed in pharmaceuticals and the typical range of pKa values they span. For instance, dexamethasone phosphate in its triprotic acid form exhibits two pKa values of 1.9 and 6.4. As a result, an aqueous solution of this compound at a dosing concentration of 40 mg/mL (pH 5.7) is capable of resisting to pH variations resulting from cathodal iontophoresis.

Figure 2A:
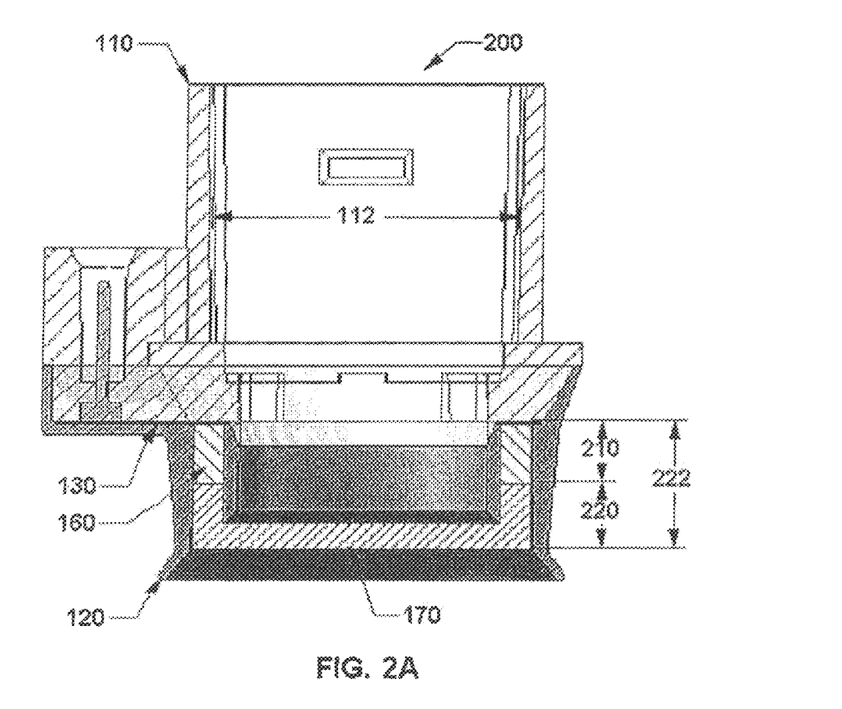
FIG. 2A shows a longitudinal cross section of a two layer buffered reservoir ocular iontophoresis device.
Figure 2B:
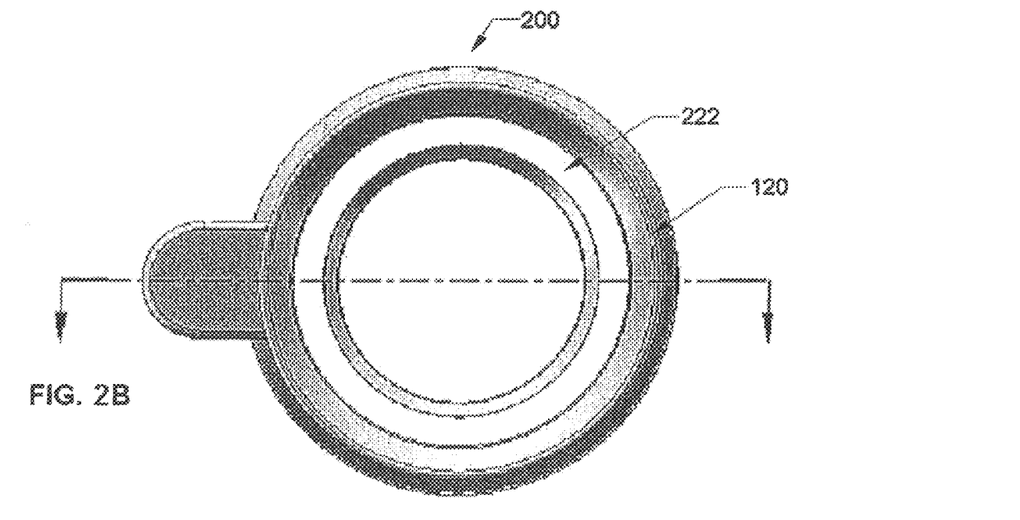
FIG. 2B shows a distal-end view of the ocular iontophoresis device shown in FIG. 2A.

FIGS. 2A-2B show a two layer buffered ocular iontophoresis device 200 for buffering a therapeutic substance to a biologically acceptable pH range at the surface of an eyeball being treated during iontophoretic treatment. In one embodiment, at least two layers 210, 220 are disposed in the annular reservoir or iontophoretic chamber 222, with at least one of the two layers including a buffering system 160. The buffer system 160 includes a buffer medium, which may be a first porous material of the first layer 210. The second layer 220 can include an API medium, which may be a second porous material for containing a therapeutic substance. In some embodiments, the buffer medium can be disposed in the second layer 220 and the API medium can be disposed in the first layer 210.

In some embodiments, the first porous material of the first layer 210 can be positioned between the second porous material of the second layer 220 and the active electrode 130. As described above, the first porous material of the first layer 210 may be saturated with a preparation (such as a liquid solution preparation and/or a liquid colloidal preparation) containing a buffer composition or a buffer composition and at least one therapeutic substance. The second porous material of the second layer 210 may be saturated with a preparation (such as a liquid solution preparation and/or a liquid colloidal preparation) containing at least one therapeutic substance. In some embodiments, the iontophoretic chamber 222 contains (i) a buffer medium made of a first porous material (e.g., an open-cell foam) containing at least one buffer element (and may or may not include a therapeutic substance) and (ii) an API medium made of a second porous material, such as, for example, an open-cell foam, containing a solution preparation of one or more therapeutic substances.

In some embodiments, the preparation may include pharmaceutically acceptable inactive ingredients for ophthalmic delivery. In some embodiments, one or both of the first porous material and the second porous material include a soluble buffer composition. In other embodiments, the first porous material and the second porous material are made of similar or different compositions. For example, the first porous material and the second porous material are made of different porous materials and/or are saturated with different preparations (in composition and/or concentration). The different preparations may include different elements, or the same elements in different concentrations.

Figure 3A:
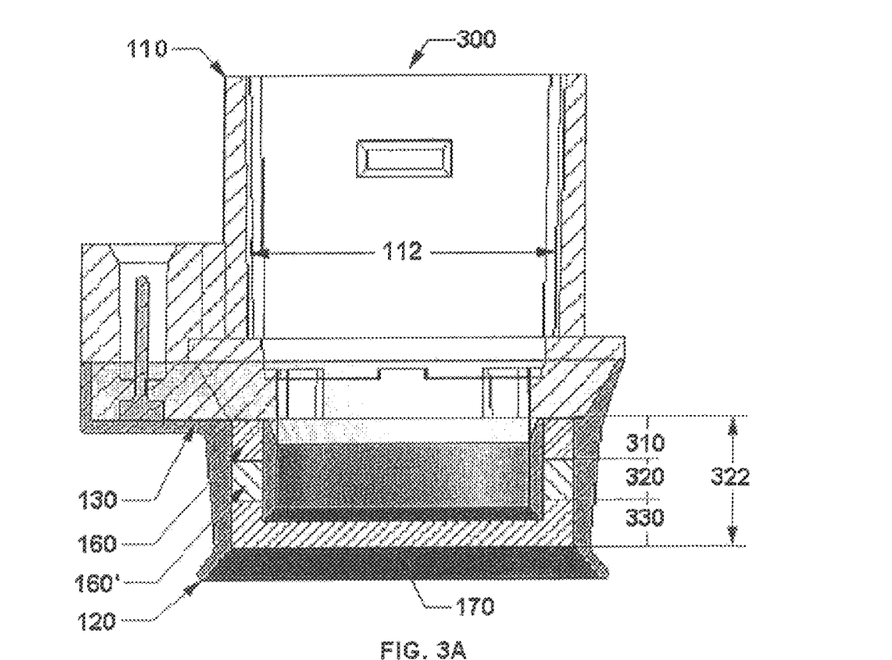
FIG. 3A shows a longitudinal cross section of a three layer buffered reservoir ocular iontophoresis device.
Figure 3B:
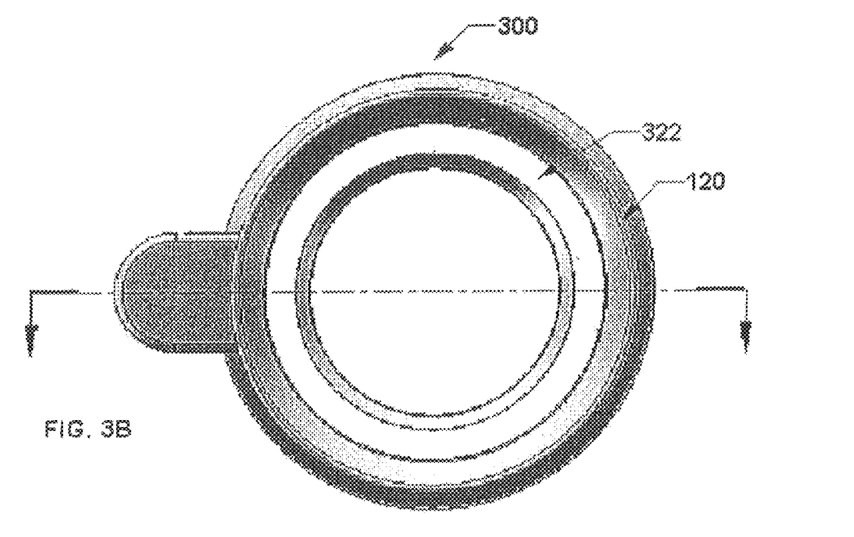
FIG. 3B shows a distal-end view of the ocular iontophoresis device shown in FIG. 3A.

FIGS. 3A-3B show a three layer buffered ocular iontophoresis device 300 for buffering a therapeutic substance to a biologically acceptable pH range at the surface of an eyeball being treated during iontophoretic treatment. In one embodiment, at least three layers 310, 320, 330 are disposed in the annular reservoir or iontophoretic chamber 322, with at least one of the three layers including a first buffering system 160 and another of the three layers including a second buffering system 160'. The first buffering system 160 includes a buffer medium, which can be a first porous material of the first layer 310. The second buffering system 160' includes a buffer medium, which can include a second porous material of the second layer 320. The third layer 320 can include an API medium, which may be a third porous material for containing a therapeutic substance. In some embodiments, the buffer mediums and the API medium can be disposed in any configuration.

In one embodiment, as shown in FIGS. 3A-3B, the first porous material of the first layer 310 can be positioned closest to the active electrode 130, the third porous material of the third layer 330 can be positioned closest to a surface of an eyeball (not shown) during use of the device 300, and the second porous material of the second layer 320 can be positioned between the first porous material and the third porous material.

In some embodiments, the first porous material and the second porous material can each include a respective buffer composition including at least one respective buffer element. For example, as discussed above, the first porous material (i.e., the porous material closest to the active electrode 130) and the second porous material may be loaded with respective buffer compositions as described above with respect to FIGS. 1A-2B. In some embodiments, the buffer system 160, 160' contains (i) a buffer medium including a first porous material (e.g., foam) and a second porous material, each containing at least one respective buffer element, and optionally containing at least one therapeutic substance, and (ii) a reservoir medium including a third porous material, such as, for example, foam, containing a solution preparation of the one or more therapeutic substances.

In some embodiments, the first porous material and the second porous material may differ in buffer composition and/or concentration of the same buffer. The first porous material and the second porous material may be made of different porous materials. In further embodiments, the third porous material may also include a buffer composition that is weaker, for example, than that of the first porous material and the second porous material. In some embodiments, the first porous material, the second porous material, and the third porous material may be made of similar or different compositions. It should be noted that any number of porous materials may be included within the buffer system.

In some embodiments, the first porous material may contain a buffer composition and the second porous material may contain an ionic composition that optimizes electrotransport of the therapeutic substance in the third porous material.

Figure 4A:
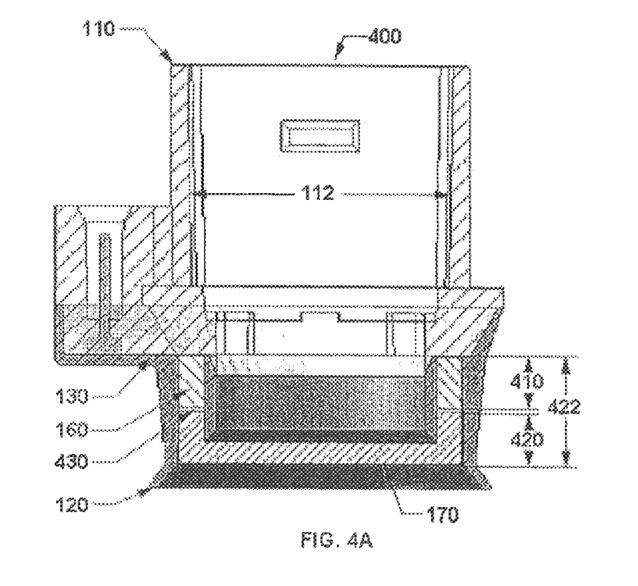
FIG. 4A shows a longitudinal cross section of a two layer buffered reservoir with membrane ocular iontophoresis device.
Figure 4B:
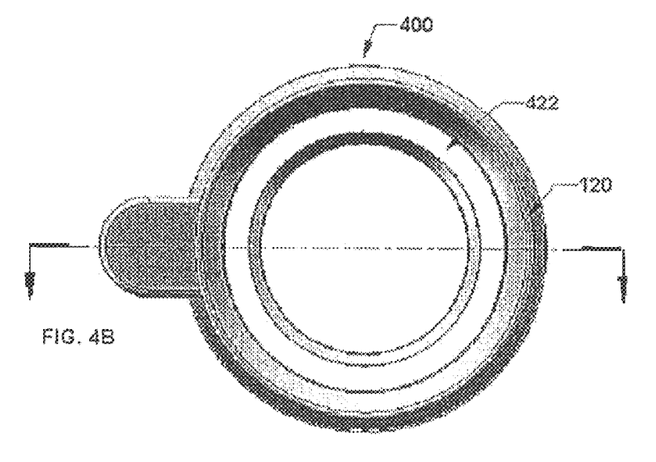
FIG. 4B shows a distal-end view of the ocular iontophoresis device shown in FIG. 4A.

FIGS. 4A-4B show a two layer buffered ocular iontophoresis device 400 with a membrane for buffering a therapeutic substance to a biologically acceptable pH range at the surface of an eyeball being treated during iontophoretic treatment. The membrane may also exhibit low water vapor permeability to maintain water content in each layer. In one embodiment, at least two layers 410, 420 are disposed in the annular reservoir or iontophoretic chamber 422, with at least one of the two layers including a buffering system 160. The buffer system 160 includes a buffer medium, which may be a first porous material of the first layer 410. The second layer 420 can include an API medium, which may be a second porous material for containing a therapeutic substance. A buffering membrane (e.g. ion exchange membrane) 430 can be disposed between the first layer 410 and the second layer 420 to provide a more stable system. In some embodiments, the buffer medium can be disposed in the second layer 420 and the API medium can be disposed in the first layer 410, while the buffering membrane 430 can be disposed before or after any of the layers.

At least one of the first porous material and the second porous material may be saturated with a preparation containing the therapeutic substance described herein. For example, the preparation may be a liquid preparation. The liquid preparation may include one or more therapeutic substances. At least one of the therapeutic substances may be dissolved in the liquid preparation. At least one of the first porous material and the second porous material may be saturated with the liquid preparation. In some embodiments, the liquid preparation may include pharmaceutically acceptable inactive ingredients for ophthalmic delivery. The first porous material and/or the second material may be buffered as discussed herein. In other embodiments, the first porous material and/or the second material may be non-buffered. In some embodiments, the liquid preparation may contain a significant amount of water. In this instance, the buffering membrane 430 may be a mono-laminar, a multi-laminar film, or hydrophobic (semi permeable) membrane in nature to retain the water content of the first layer 410 for stability.

In some embodiments, a mono-laminar or a multi-laminar ion-exchange film or membrane may be placed in the iontophoretic chamber 422 in contact or approximately near the active electrode 130. In further embodiments, the membrane may be rolled or otherwise disposed in an annular space of the iontophoretic chamber 422 in one piece or multiple pieces. In some embodiments, the iontophoretic chamber 422 may be filled with multiple small membrane pieces. In further embodiments, the membrane may be laminated along with the porous material matrix.

Figure 5A:
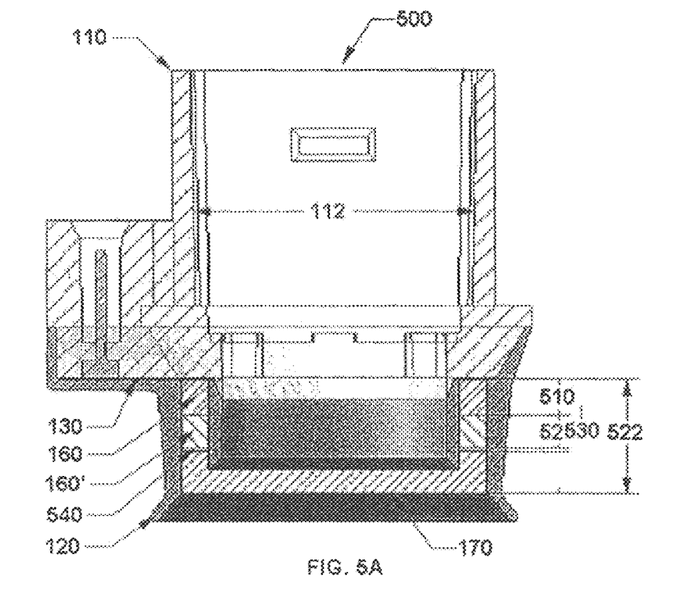
FIG. 5A shows a longitudinal cross section of a three layer buffered reservoir with membrane ocular iontophoresis device.
Figure 5B:
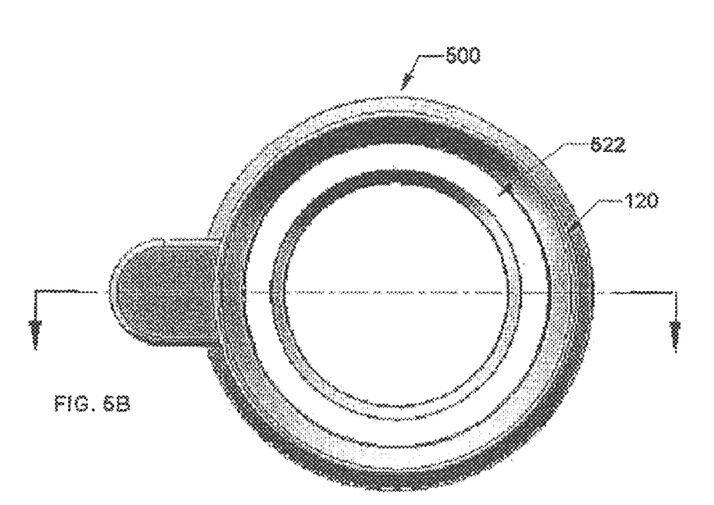
FIG. 5B shows a distal-end view of the ocular iontophoresis device shown in FIG. 5A.

FIGS. 5A-5B show a three layer buffered ocular iontophoresis device 500 with membrane for buffering a therapeutic substance to a biologically acceptable pH range at the surface of an eyeball being treated during iontophoretic treatment. In one embodiment, at least three layers 510, 520, 530 are disposed in the annular reservoir or iontophoretic chamber 522, with at least one of the three layers including a first buffering system 160 and another of the three layers including a second buffering system 160'. The first buffering system 160 includes a buffer medium, which can be a first porous material of the first layer 510. The second buffering system 160' includes a buffer medium, which can include a second porous material of the second layer 520. The third layer 530 can include an API medium, which may be a third porous material for containing a therapeutic substance. In some embodiments, the buffer mediums and the API medium can be disposed in any configuration. A buffering membrane (e.g. ion exchange membrane) 540 can be disposed between the second layer 510 and the third layer 530 to provide a more stable system. Another buffering membrane (not shown) can be disposed between the first layer 510 and the second layer 520. In some embodiments, the buffer medium can be disposed in the second layer 520 and the API medium can be disposed in the second layer 520, while the buffering membrane 540 can be disposed before or after any of the layers. In some embodiments, the first layer 510 may contain a buffer composition and the second layer 520 may contain an ionic composition that optimizes electro-transport of the therapeutic substance in the third porous material.

Figure 6A:
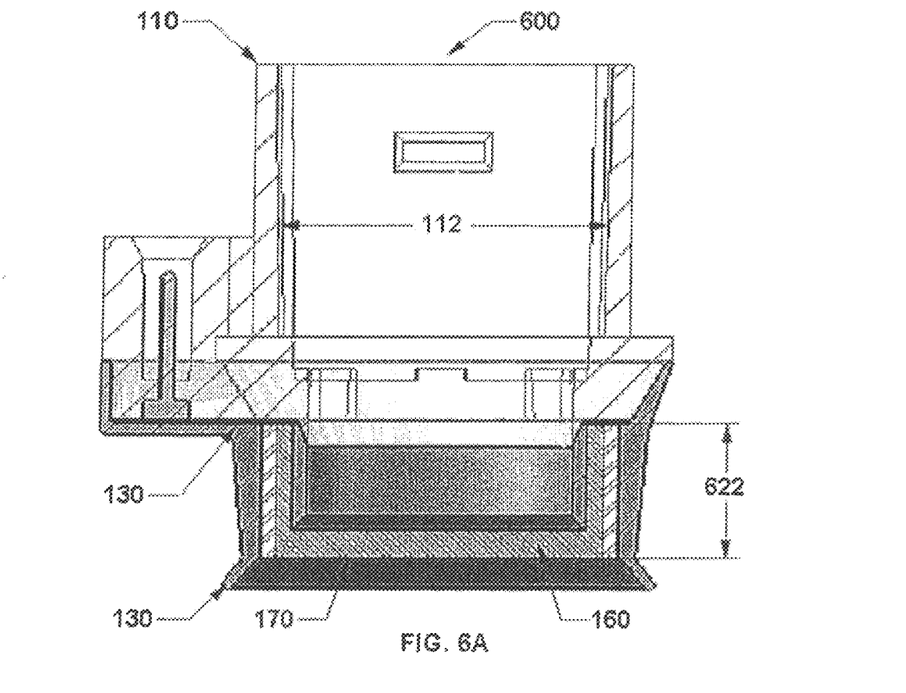
FIG. 6A shows a longitudinal cross section of a two concentric layer buffered reservoir ocular iontophoresis device.
Figure 6B:
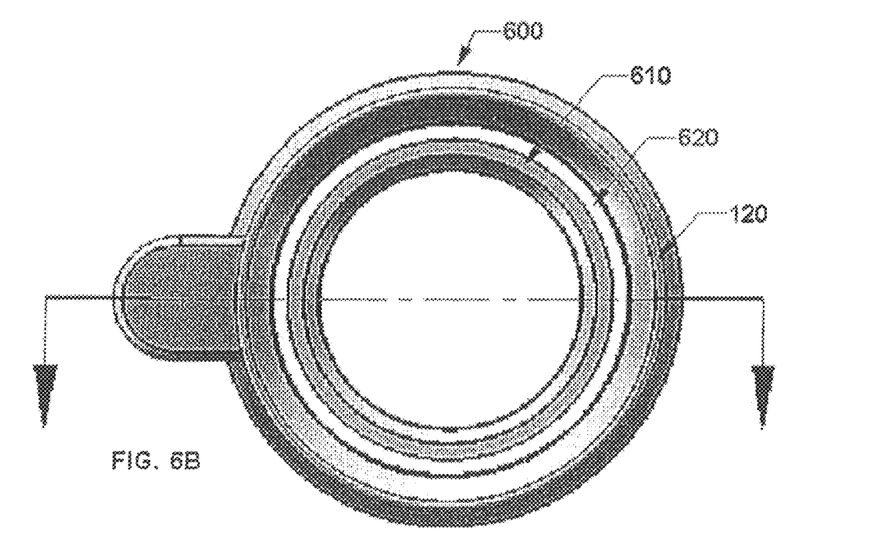
FIG. 6B shows a distal-end view of the ocular iontophoresis device shown in FIG. 6A.

FIGS. 6A-6B show two concentric layer buffered ocular iontophoresis device 600 for buffering a therapeutic substance to a biologically acceptable pH range at the surface of an eyeball being treated during iontophoretic treatment. In one embodiment, at least two layers 610, 620 are disposed in the annular reservoir or iontophoretic chamber 622 as concentric rings, with at least one of the two layers including a buffering system 160. The buffer system 160 includes a buffer medium, which may be a first porous material of the first layer 610. The second layer 620 can include an API medium, which may be a second porous material for containing a therapeutic substance. In some embodiments, the buffer medium can be disposed in the second layer 620 and the API medium can be disposed in the first layer 610. In some embodiments, multiple layers of concentric rings can be disposed in the annular reservoir or iontophoretic chamber 622 with any configuration of mediums (e.g., buffer and/or API).

In some embodiments, the first porous material can be saturated with a preparation (such as a liquid solution preparation and/or a liquid colloidal preparation) containing a buffer composition and a therapeutic substance. In some embodiments, the buffer system 160 contains (i) a buffer medium made of a first porous material (e.g., foam) containing at least one buffer element, and optionally containing at least one therapeutic substance, and (ii) a therapeutic reservoir medium made of a second porous material, such as, for example, foam, containing a solution or a colloidal preparation of one or more therapeutic substances, with the buffer medium being concentrically arranged within the API medium.

In some embodiments, one or more of the therapeutic and buffer preparations may include pharmaceutically acceptable inactive ingredients for ophthalmic delivery. In some embodiments, one or both of the first porous material and the second porous material may include a soluble buffer composition. In various embodiments, the first porous material and the second porous material may be made of similar or different compositions. In further embodiments, the second porous material may include a buffer composition that is weaker, for example, than that of the first porous material.

In various other embodiments, the layers 610, 620 containing the buffer medium and the API medium (including various porous materials of each) may be arranged, shaped, or otherwise configured in any suitable arrangement, such as, but not limited to, a semi-circular API medium complementing a semi-circular buffer medium, and alternating layers of API mediums and buffer mediums.

Figure 7:
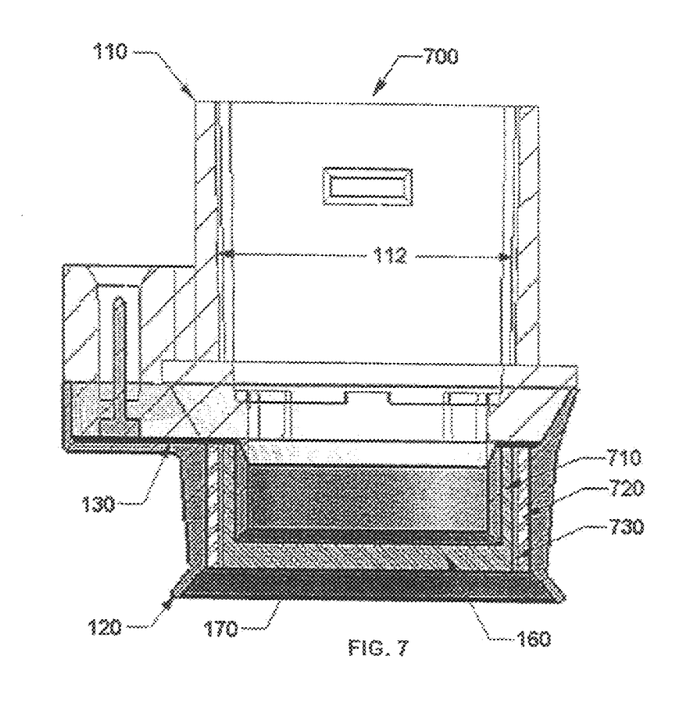
FIG. 7 shows a longitudinal cross section of a two concentric layer buffered reservoir with membrane ocular iontophoresis device.

FIG. 7 shows two concentric layer buffered ocular iontophoresis device 700 for buffering a therapeutic substance to a biologically acceptable pH range at the surface of an eyeball being treated during iontophoretic treatment. In one embodiment, at least two layers 710, 720 are disposed in the annular reservoir or iontophoretic chamber 722 as concentric rings, with at least one of the two layers including a buffering system 160. The buffer system 160 includes a buffer medium, which may be a first porous material of the first layer 710. The second layer 720 can include an API medium, which may be a second porous material for containing a therapeutic substance. A membrane 730 can be disposed between the first layer 710 and the second layer 720 to provide a more stable system. In some embodiments the membrane 730 is a buffering membrane (e.g. ion exchange membrane). In other embodiments the membrane 730 may be a solid partition. In some embodiments, the buffer medium can be disposed in the second layer 720 and the API medium can be disposed in the first layer 710, while the buffering membrane 730 can be disposed before or after any of the layers. In some embodiments, multiple layers of concentric rings can be disposed in the annular reservoir or iontophoretic chamber 622 with any configuration of mediums (e.g., buffer and/or API) or buffering membranes.

Figure 8:
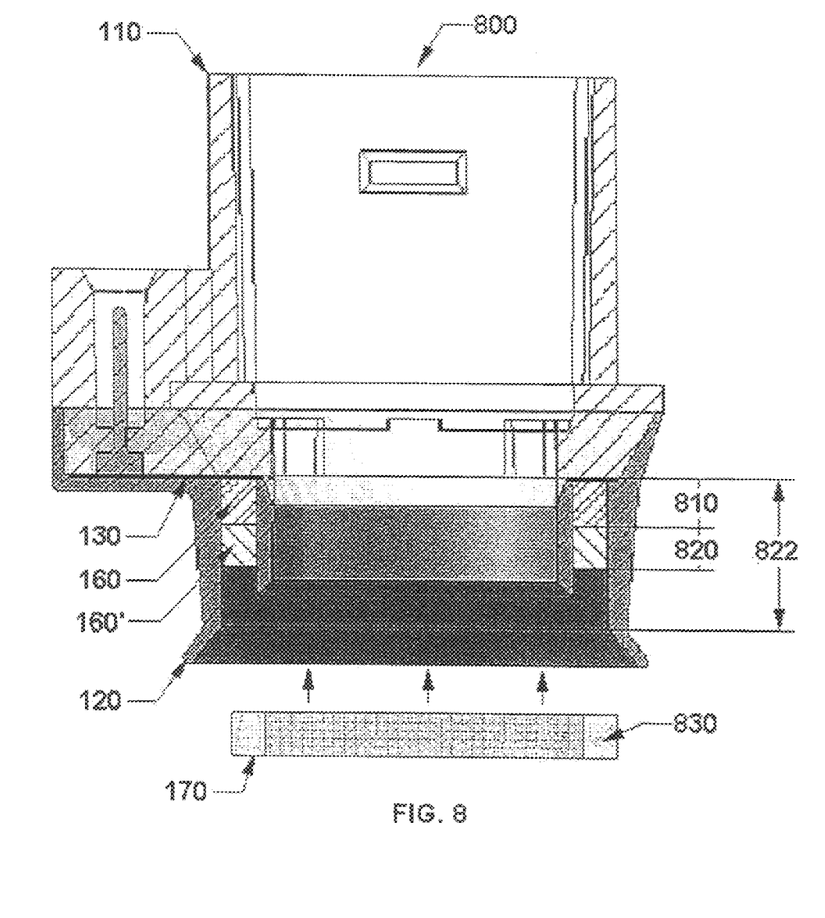
FIG. 8 shows a longitudinal cross section of a three layer buffered reservoir with drug loaded ring ocular iontophoresis device.

FIG. 8 shows a three layer buffered ocular iontophoresis device 800 for buffering a therapeutic substance to a biologically acceptable pH range at the surface of an eyeball being treated during iontophoretic treatment. In one embodiment, at least three layers 810, 820, 830 are disposed in the annular reservoir or iontophoretic chamber 822, with at least one of the three layers including a first buffering system 160 and an optionally another layer including a second buffering system 160'. The first buffering system 160 includes a buffer medium, which can be a first porous material of the first layer 810. The second buffering system 160' includes a buffer medium, which can include a second porous material of the second layer 820. The third layer 830 can include an API medium, which may be a third porous material for containing a therapeutic substance.

In some embodiments, the third layer 830 containing the API medium is supplied separate from the iontophoresis device 800. In these instances, the end user combines the third layer 830 with the iontophoresis device 800 just prior to use.

In some embodiments, the iontophoretic chambers 122-822 may include a rehydrating agent that may be added to at least one of the buffer medium and/or API medium to facilitate homogeneous hydration within the film/membrane.

It should be understood that buffer medium(s), alone or in combination, described in any of the above embodiment (FIGS. 1A-8) can be a porous material (with or without a solution or colloidal dispersion), a gel (e.g., liquid gel, solid gel), and/or a buffering resin (e.g., a packed base resin).

The gel may include one or more buffer elements. In some embodiments, the buffer medium also includes at least one therapeutic substance together with a buffer composition. At least one of the therapeutic substances may be dissolved within the gel. In some embodiments, the buffer system includes a therapeutic reservoir medium made of a gel containing one or more therapeutic substances and a buffer. In some embodiments, the gel may include pharmaceutically acceptable inactive ingredients for ophthalmic delivery.

In some embodiments, the buffer system may further include a buffer medium having a gel including a soluble buffer composition. In other embodiments, such as in a case where the therapeutic substance is a drug that has "self-buffering" capabilities, the gel may not require a separate buffer composition.

In other embodiments, at least one of the therapeutic substances may be insoluble in the gel. Accordingly, the therapeutic substances may exist as nanometer-sized particulates, for example. In yet other embodiments, at least one of the therapeutic substances may be encapsulated in nanometer-sized particulates, for example.

In some embodiments, the buffer composition may include ion exchange resin particles that may include cation and/or anion exchange resins. In some embodiments, the buffer composition includes polymeric particles that may include cationic and/or anionic particles. In some embodiments, the buffer composition includes insoluble buffer substance particles of polymeric or non-polymeric nature. The particles may have regular shapes (e.g., round, spherical, cube, cylinder, fiber, cone, needle, and the like), irregular shapes, or a combination of regular and irregular shapes.

In some embodiments, the therapeutic composition may be a liquid colloidal preparation. The liquid colloidal preparation may include one or more therapeutic substances. In some embodiments, the liquid colloidal preparation may include pharmaceutically acceptable inactive ingredients for ophthalmic delivery. At least one of the therapeutic substances may be insoluble in the liquid colloidal preparation. Accordingly, the therapeutic substances may exist as nanometer-sized particulates, for example. In yet other embodiments, at least one of the therapeutic substances may be encapsulated in nanometer-sized particulates, for example. In other embodiments, the medium may be a gel, containing the therapeutic substance.

In some embodiments, the buffered therapeutic preparation may be a liquid colloidal preparation. The liquid colloidal preparation may include one or more therapeutic substances and a buffer composition. In some embodiments, the liquid colloidal preparation may include pharmaceutically acceptable inactive ingredients for ophthalmic delivery. At least one of the therapeutic substances may be insoluble in the liquid colloidal preparation. Accordingly, the therapeutic substances may exist as nanometer-sized particulates, for example. In yet other embodiments, at least one of the therapeutic substances may be encapsulated in nanometer-sized particulates, for example. In other embodiments, the API medium may be a gel for containing the therapeutic substance.

In various embodiments, the therapeutic substance may be in a form of a free drug (i.e., non-encapsulated or non-dissolved). In other embodiments, the therapeutic substance may be in a form of nano-particles or may be nano-encapsulated.

In various embodiments, the therapeutic substance may be present in the iontophoretic chamber in an aqueous solution, or dispersed or dissolved in a liquid or solid gel.

In various embodiments, encapsulated drug nanoparticles may include at least one of nanospheres, nanocapsules, coated nanospheres, and coated nanocapsules. As used herein, nanometer-sized particles, nano-particles, nanocapsules, nanospheres and the like refer to structures having sub-micron dimensions. For example, nanometer-sized structures may be dimensioned no larger than 100 nm, or tens of nanometers, or even smaller.

Porous materials provided in various embodiments, such as any of those described above, can include an open cell porous material. Such an open cell porous material may include, but not be limited to, foam, fabric, nonwoven material, and/or sintered material that contain a buffer in at least one of its components. In other embodiments, the porous material is made of, but is not limited to polyethylene, polyurethane, polypropylene, PTFE, PVDF, EVA, nylon, ceramic, and the like.

Gels provided in various embodiments, such as any of those described above, can include any type of gel, including solid or liquid gels that contain a buffer as one of its components. The gel may be made of, but is not limited to, carbomer homopolymers (Type A, B, and C), polyethylene glycols, polyvinyl alcohol (PVA), methylcellulose, carboxymethyl cellulose (CMC), hydroxypropyl cellulose (HPC), hydroxypropylmethyl cellulose (HPMC), hydroxyethyl cellulose (HEC), alginate, gellan gum, xanthan gum, agarose, and the like.

In some embodiments, the resin, such as a packed bed resin, for example, is any type of ion exchange resin packed as a layer in the iontophoretic chamber. The ion exchange resins may have buffering capabilities and may be located as a layer contained in porous material, for example. The resin may be made of, but is not limited to, anion exchange resins and cation exchange resins, either of which may be characterized by having a strong acid, strong base, weak acid, and weak base.

In some embodiments, the buffer composition includes ion exchange resin particles that may include cation and/or anion exchange resins. In some embodiments, the buffer composition may include polymeric particles that may, in turn, include cationic and/or anionic particles. In some embodiments, the buffer composition may be a plurality of insoluble buffer substance particles of polymeric or non-polymeric nature. The particles may have regular shapes (e.g., round, spherical, cube, cylinder, fiber, cone, needle, and the like), irregular shapes, or combinations of regular and irregular shapes.

In some embodiments, the membrane is made of any material that has buffering capabilities. The membrane may be made of, but is not limited to, for example, amino methacrylate copolymer, methacrylic acid copolymers (Type A and B), HPMCAS (hydroxypropyl methylcellulose acetate succinate), CAP (cellulose acetate phthalate) and the like. The membrane may be made of, but is not limited to, anion exchange resins and cation exchange resins, either of which may be characterized by having a strong acid, strong base, weak acid, and weak base. In some embodiments, the membrane may be semi-permeable to allow passage of selective therapeutic substances, but not other inactive ingredients as described herein.

In some embodiments, the buffer composition of the membrane includes ion exchange resin particles that may include cation and/or anion exchange resins. In some embodiments, the buffer composition of the membrane may include polymeric particles that may, in turn, include cationic and/or anionic particles. In some embodiments, the buffer composition of the membrane may be a plurality of insoluble buffer substance particles of polymeric or non-polymeric nature. The particles may have regular shapes (e.g., round, spherical, cube, cylinder, fiber, cone, needle, and the like), irregular shapes, or a combination of regular and irregular shapes.

In some embodiments, the buffering medium may include a buffering element or agent (or a composition having a buffering agent), such as, but not limited to a polymeric buffering agent. The polymeric buffering agent may be suitable for regulating the pH of a preparation containing the therapeutic substance (i.e., drug preparation) within a given pH range during iontophoresis. The polymeric buffering agent may be any polymer that ionizes at a given pH by consuming hydrogen ions or hydroxyl ions and maintains a pH of the preparation in the iontophoretic chamber within a desired range.

In some embodiments, the buffering agent may be a polymeric buffer that cannot pass through the buffer medium of the device to the therapeutic medium containing the therapeutic substance in the iontophoretic chamber. Because of the large molecular size of the polymeric buffer, an ionized polymeric buffering agent has low ionic mobility and does not significantly compete with the preparation containing the therapeutic substance or fluid ions for carrying electric charge. Therefore, the polymeric buffering agent does not decrease compound delivery efficiency.

In some embodiments, the polymeric buffering agent may have a molecular weight sufficiently high to prevent passage of the polymeric buffering agent to the eyeball surface. The polymeric buffering agent may be water soluble or water insoluble. For example, in one embodiment, the polymeric buffering agent may be a water insoluble polymeric buffer in a form of fine particles to maximize its surface area. Furthermore, the buffer medium may include small particles of the polymeric buffering agent suspended in a hydrogel membrane. In other embodiments, the water insoluble polymeric buffering agent may be formed into a porous polymer membrane that may cover the active electrode and/or the internal wall of the iontophoretic chamber and/or the porous material. The porous polymer membrane may also be used as a semi-permeable membrane.

In some embodiments, the polymeric buffering agent may be an ion exchange resin that may be selected from, but not limited to, the following group: methacrylic acid/divinyl-benzene copolymers and styrene/divinylbenzene copolymers, and the like. Methacrylic acid/divinylbenzene polymers have weak acid (carboxyl group) functionality and are available in hydrogen or potassium form. Styrene/divinylbenzene polymers have either strong acid (sulfonate group) or strong base (tertiary amine group) functionality. The former resins may be available in hydrogen, sodium or calcium form and the latter resins may be available in chloride form. The ion exchange resins are commercially available in a powder, granular, or fiber form, or as a membrane, or the like.

In some embodiments, the buffer composition may include an amino acid buffer or a combination of amino acids with cationic behavior. Amino acids with cationic behavior are positively charged and may be used for cathodic iontophoresis. In such embodiments, the electrotransport of buffer cations through the eye can be reduced or eliminated. A poorly transported buffer may help to avoid depletion of the buffer composition from the iontophoretic chamber as well as any irritation associated with buffer cations being transported into the eye tissues. In other embodiments, the cathodic iontophoresis may be buffered using an anionic or negatively charged acid buffer. In further embodiments, mixtures of a cationic amino acid buffer and an anionic acid buffer may also be used.

Concentration of the buffer composition required in the cathodic reservoir may depend, for example, on the properties of a specific buffer selected. Cationic amino acids may be selected from (but not limited to) the following group: arginine, aspartic acid, cysteine, glutamic acid, histidine, lysine, and tyrosine. Anionic acids may be selected from (but not limited to) the following group: acetic acid, adipic acid, aspartic acid, benzoic acid, citric acid, ethylenediamine tetracetic acid, formic acid, fumaric acid, glutamic acid, glutaric acid, maleic acid, malic acid, malonic acid, phosphoric acid, and succinic acid.

In some embodiments, the buffer composition may include an amino acid buffer or a combination of amino acids with anionic behavior. Amino acids with anionic behavior are negatively charged and may be used for anodic iontophoresis. In some embodiments buffers may include zwitterions. In some embodiments, the anodic iontophoresis may be buffered using an anionic acid. In such embodiments, competition between the anodic buffer and the therapeutic substance (i.e., the drug formulation) for delivery into the eyeball may be reduced or eliminated. In other embodiments, the anodic iontophoresis may be buffered using a cationic or positively charged base buffer, or an amino acid displaying cationic behavior at the reservoir pH. In further embodiments, mixtures of an anionic acid buffer and a cationic base or amino acid buffer may also be used.

Concentration of buffer composition required in the anodic reservoir depends on the properties of a specific buffer selected. Anionic amino acids may be selected from (but are not limited to) the following group: cysteine, histidine, and tyrosine. Zwitterions may be selected from (but are not limited to) the following group: N-2(2-acetamido)-2-aminoethane sulfonic acid [ACES], N-2-acetamido iminodiacetic acid [ADA], N,N-bis(2-hydroxyethyl)-2-aminoethane sulfonic acid [BES], 2-[Bis-(2-hydroxyethyl)-amino]-2-hydroxymethyl-propane-1,3-diol [Bis-Tris], 3-cyclohexylamino-1-propane sulfonic acid [CAPS], 2-cyclohexylamino-1-ethane sulfonic acid [CHES], N,N-bis(2-hydroxyethyl)-3-amino-2-hydroxypropane sulfonic acid [DIPSO], 4-(2-hydroxyethyl)-1-piperazine propane sulfonic acid [EPPS], N-2-hydroxyethylpiperazine-N'-2-ethane sulfonic acid [HEPES], 2-(N- morpholino)-ethane sulfonic acid [MES], 4-(N-morpholino)-butane sulfonic acid [MOBS], 2-(N-morpholino)-propane sulfonic acid [MOPS], 3-morpholino-2-hydroxypropanesulfonic acid [MOPSO], 1,4-piperazine-bis-(ethane sulfonic acid) [PIPES], piperazine-N,N'-bis(2-hydroxypropane sulfonic acid) [POPSO], N-tris (hydroxymethyl)methyl-2-aminopropane sulfonic acid [TAPS], N-[tris(hydroxymethyl)methyl-3-amino-2-hydroxypropane sulfonic acid [TAPSO], N-tris(hydroxymethyl)methyl-2-aminoethane sulfonic acid [TES], and 2-Amino-2-hydroxymethyl-propane-1,3-diol [Tris]. Anionic acid buffers may be selected from (but are not limited to) the following group: acetic acid, adipic acid, benzoic acid, carbonic acid, citric acid, ethylenediamine tetracetic acid, fumaric acid, glutamic acid, lactic acid, maleic acid, malic acid, malonic acid, phosphoric acid, tartaric acid, and succinic acid. Cationic bases and amino acids may be selected from (but are not limited to) the following group: arginine, histidine, imidazole, lysine, triethanolamine, and tromethamine.

In some embodiments, the buffer composition may be a cross-linked polymer or a combination of polymers with anionic or cationic behavior. Although not necessarily so limited, the polymeric buffers used in the cathodic iontophoresis may be those displaying anionic behavior whereas the polymeric buffers used in the anodic iontophoresis may be those displaying cationic behavior. The use of polymeric buffers eliminates or minimizes competition from buffer ions and/or counter ions, for example, with the therapeutic substance for delivery to the eyeball.

In some embodiments, the buffer composition may be a polymer or a combination of polymers with anionic or cationic behavior. Although not necessarily so limited, the polymeric buffers used in the cathodic iontophoresis may be those displaying anionic behavior whereas the polymeric buffers used in the anodic iontophoresis may be those displaying cationic behavior. The use of polymeric buffers eliminates or minimizes competition from buffer ions and or counter ions, for example, with the therapeutic substance for delivery to the eyeball.

The anionic polymer may be selected from (but is not limited to) the following group: poly(acrylic acid), poly (acrylic acid) cross-linked with polyalkenyl ethers or divinyl glycol, poly(methacrylic acid), styrene/maleic anhydride copolymers, methyl vinyl ether/maleic anhydride copolymers, poly(vinyl acetate phthalate), cellulose acetate phthalate, cellulose acetate trimellitate, hydroxypropyl methylcellulose acetate succinate, ethyl acrylate/methacrylic acid copolymers, methyl methacrylate/methacrylic acid copolymers, and alginic acid, and the like. The cationic polymer may be selected from (but is not limited to) the following group: polyvinylpyridine, methyl methacrylate/butyl methacrylate/dimethylaminoethyl methacrylate terpolymers, vinylpyrrolidone/quaternized dimethyl aminoethyl methacrylate copolymers, vinylcaprolactam/vinylpyrrolidone/dimethyl aminoethyl methacrylate terpolymers, and chitosan, and the like.

In some embodiments, the buffer composition may be a low molecular weight compound with anionic or cationic behavior. Although not necessarily so limited, the buffers used in the cathodic iontophoresis may be those displaying anionic behavior whereas the buffers used in the anodic iontophoresis may be those displaying cationic behavior. Examples of this type of buffer can include, but are not limited to, sodium/potassium acetate, sodium/potassium citrate, and/or all of the "Good's buffers," which includes MES, ADA, PIPES, ACES, BES, TES, HEPES, cholamine chloride, acetomidoglycine, tricine, glycinamide, and bicine.

In various embodiments, at least one buffer element or agent may be incorporated into the buffer medium through (i) chemical bonding (e.g., the buffer agent may be covalently bonded to the buffer medium); (ii) physical bonding (e.g., an electrostatic charge of buffer binds it to the buffer medium); (iii) mechanical bonding (e.g., a size of the buffer material may be larger than a pore size of the buffer medium, thus trapping the buffer material in the reservoir); (iv) coating (e.g., the buffer medium may be coated with buffered material); (v) emulsion (e.g., a liquid buffer may be suspended in a liquid reservoir); and (vi) solid suspension (e.g., a buffer is suspended in a solid reservoir).

In various embodiments, the addition of many of the above described buffer mediums and/or buffer compositions may reduce available space of a therapeutic reservoir medium used to house the therapeutic substance (or active pharmaceutical ingredient (API)) containing preparation. As a result, an overall volume needed to fill the API medium may be reduced. For example, an approximately 3-mm thick gel/membrane buffer system may result in an overall reduction of needed API containing solution by at least half. Each 1 mm of porous material replaced by a gel/membrane buffer system from the iontophoretic chamber may result in a 16% reduction in API containing solution needed to fill the API medium. As another example, an iontophoretic chamber having a foam insert (API medium) of approximately 1-2 mm requires only 100-300 μL of API containing solution. A secondary result of the additional buffer mediums is that the distance of the active electrode is extended from the ocular surface creating and added safety benefit.

The embodiments disclosed herein are to be considered in all respects as illustrative, and not restrictive of the invention. The technology described herein is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:
1. A delivery device for transferring a therapeutic substance across and/or through a surface of an ocular globe, comprising:
   an iontophoretic chamber configured to store the therapeutic substance;
   an electrode disposed relative to the iontophoretic chamber, the electrode configured to provide an electromotive force, when energized, to transfer of at least a portion of the therapeutic substance stored within the iontophoretic chamber across and/or through the surface of the ocular globe;
   a buffer system disposed at least partially within the at least one iontophoretic chamber, the buffer system does not contain the therapeutic substance, the buffer system configured to maintain a pH at the surface of the ocular globe within a range of about 3 to 8 during iontophoretic transfer of the therapeutic substance; and
   the iontophoretic chamber further comprises a first layer and a second layer, the first layer including the buffer system and the second layer including a therapeutic substance, wherein the first layer is disposed closest to the electrode and has a higher buffering capacity than the second layer.

2. The delivery device of claim 1, wherein the buffer system includes a buffering agent to reduce the risk of damage to ocular tissue.

3. The delivery device of claim 2, wherein the buffer agent comprises at least one of an ion exchange resin, polymeric particles, insoluble buffer particles, cationic particles, anionic particles and zwitterionic particles.

4. The delivery device of claim 3, wherein the ion exchange resin comprises at least one ion exchange material having a characteristic nature of at least one of a strong acid, a strong base, a weak acid, and a weak base.

5. The delivery device of claim 2, wherein the buffer system further comprises a therapeutic substance.

6. The delivery device of claim 1, wherein the pH is maintained at a level substantially equal to the highest ionization level of the therapeutic substance to enhance transport efficiency of the therapeutic substance.

7. The delivery device of claim 1, wherein the buffer system is electrically conductive capable of conducting an electric field supplied from the electrode.

8. The delivery device of claim 1, wherein buffer system includes at least one of a porous material, a liquid solution, a gel, a packed bed resin, a hydro gel film, and a membrane.

9. The delivery device of claim 8, wherein the porous material comprises at least one of a foam, a fabric, a nonwoven material, and a sintered material.

10. The delivery device of claim 8, wherein of the gel comprises at least one of a hydrogel matrix and an aerogel matrix.

11. The delivery device of claim 8, wherein the membrane comprises at least one of a mono-laminar, a multi-laminar film, hydrophobic (semi permeable) membrane, and a non-permeable/solid membrane.

12. The delivery device of claim 1, further comprising a membrane disposed between the first layer and the second layer.

13. The delivery device of claim 12, wherein the membrane has low water vapor permeability to maintain water content in each layer.

14. The delivery device of claim 1, wherein the layers are arranged concentrically relative to each other.

15. The delivery device of claim 14, further comprising a membrane disposed between the first layer and the second layer.

16. The delivery device of claim 1, wherein the buffer system is arranged as a buffered surface coating.

17. The delivery device of claim 1, wherein the buffer system further comprises a rehydrating agent.

18. The delivery device of claim 1, wherein the buffer system is disposed adjacent to the electrode.

19. The delivery device of claim 1, wherein a third layer is disposed between the first layer and the second layer, the third layer further including the buffer system.

* * * * *